United States Patent [19]
Servidio et al.

[11] Patent Number: 5,117,819
[45] Date of Patent: Jun. 2, 1992

[54] NASAL POSITIVE PRESSURE DEVICE

[75] Inventors: John L. Servidio; Robert E. Tucker, both of Marietta, Ga.

[73] Assignee: Healthdyne, Inc., Marietta, Ga.

[21] Appl. No.: 579,900

[22] Filed: Sep. 10, 1990

[51] Int. Cl.$^5$ ............................................ A61M 16/00
[52] U.S. Cl. .............................. 128/204.18; 128/204.21
[58] Field of Search ................ 128/204.21, 204.23, 128/205.25, 205.24, 207.13, 204.18

[56] References Cited

U.S. PATENT DOCUMENTS

| | | | |
|---|---|---|---|
| 3,044,464 | 7/1962 | Gray | 128/205.25 |
| 4,587,967 | 5/1986 | Chu et al. | 128/204.21 |
| 4,655,213 | 4/1987 | Rapoport et al. | 128/205.25 |
| 4,665,911 | 5/1987 | Williams et al. | 128/204.23 |
| 4,686,975 | 8/1987 | Naimon et al. | 128/204.23 |
| 4,807,616 | 2/1989 | Adahan | 128/204.21 |
| 4,944,310 | 7/1990 | Sullivan | 128/205.25 |
| 4,957,107 | 9/1990 | Sipin | 128/204.21 |

FOREIGN PATENT DOCUMENTS

82/03548 10/1982 World Int. Prop. O. .

OTHER PUBLICATIONS

Healthdyne, "Tranquility Nasal Cap System".

Primary Examiner—Edgar S. Burr
Assistant Examiner—Aaron J. Lewis
Attorney, Agent, or Firm—Foley & Lardner

[57] ABSTRACT

A device treats sleep apnea by supplying pressurized air to the nasal passages of a user through a connection device connected to said control device through a hose. The device includes a blower which pressurizes air and which supplies the pressurized air to the connection device, and a control device adapted to control the pressure level supplied by the generating device. The control device incudes a ramp generating device adapted to selectively control the generating device to generate pressurized air at a pressure level which increases for a preset time to a preset prescribed pressure level, and an override device which, when actuated, overrides the ramp generating device and which controls the generating device to immediately generate pressurized air at the preset prescribed pressure level.

31 Claims, 3 Drawing Sheets

NASAL POSITIVE PRESSURE DEVICE

BACKGROUND OF THE INVENTION

1. Field of the Invention

The invention relates to a medical device for treating sleep apnea, specifically a nasal continuous positive airway pressure (CPAP) device. CPAP involves the administration of air under pressure to a patient through a mask or any other suitable connection means. The positive air pressure from the CPAP device forces the upper respiratory tract open, prevents collapse of the pharynx and tongue over the air passage, and aids in increasing lung volume which improves the upper airway muscle dilation tone as air is exhaled.

2. Description of the Prior Art

Sleep apnea syndrome is a sleep disorder characterized by recurrent, prolonged episodes of apnea (cessation of breathing) throughout the night causing excessive daytime sleepiness (hypersomnolence). While occasional periods of apnea during sleep are relatively harmless and occur in most adults, those suffering from sleep apnea syndrome experience episodes of breathing obstruction that last more than 10 seconds and which occur an average of 5 times per hour. Many sleep apnea patients experience apneic periods lasting more than 30 seconds, and have hundreds of such episodes throughout the night causing them to spend most of the night in airway obstruction.

Three types of sleep apnea occur:
1. obstructive sleep apnea, in which breathing is blocked by an obstruction of the upper respiratory tract producing respiratory effort, but no air flow,
2. central sleep apnea, a less common condition, in which the respiratory signals from the brain temporarily cease to stimulate respiratory effort, and
3. mixed sleep apnea, in which elements of both obstructive and central sleep apnea are present, usually as a central component followed by an obstructive component.

A number of conditions are thought to contribute to the sleep apnea syndrome. As would be expected, obstructive sleep apnea is associated with factors that would easily cause obstruction of the upper respiratory tract. There are four major factors contributing to obstructive sleep apnea. Poor muscle tone in the muscles lining the upper airway results in inadequate muscle tone to assist in keeping the airway open during inspiration. The presence of abnormal structures that impinge on airways such as large adenoids and tonsils in children, or bulky pharyngeal tissues in obese adults may reduce airway space, and patients with malformations of the chin, or with enlarged tongues may not be able to accommodate their tongues, causing them to fall back and block the airway. Excessive length of the soft palate and uvula results in reduction in the nasopharyngeal space and reduction in air flow. Restricted air flow through the nose creates increased negative pressure during inspiration which draws together the flaccid tissues in the collapsible part of the airway.

Several devices have been used to treat obstructed sleep apnea. Nasopharyngeal tubes have been developed which are inserted into the upper airway to reach past the point of obstruction in order to maintain upper airway patency during sleep. While they do work, nasopharyngeal tubes are extremely uncomfortable, and most patients cannot tolerate them on a long-term basis.

A number of tongue restraining devices (TRDs) have been developed to prevent the tongue from obstructing the airway during sleep. One newer TRD acts to pull the tongue away from the posterior wall of the pharynx, and appears to relieve sleep apnea to some degree in some patients. Investigators are unsure if patients will comply with long-term TRD therapy, and speculate that it may serve as a noninvasive method for temporary relief of apnea while patients are attempting weight reduction and other behavior modification changes.

There have been several surgical approaches to try to diminish the severity of obstructive sleep apnea. Tracheostomy, for example, was one of the first approaches to surgically treat apnea. In this procedure, a tracheostomy tube bypasses the airway obstruction and allows a patient to breathe. Another surgical procedure, called Uvulopalatopharyngoplasty or UPPP, removes redundant tissue in the patient's airway. The UPPP is a relatively new surgical approach which is currently being documented for its effectiveness. Another technique, Maxillomandibular and hyoid advancement, is a complicated multifaceted surgery that is presently being documented in medical journals. Although this particular type of surgery looks encouraging, its practice will be limited due to the cost and preclusion criteria for the surgery. The cost of surgery and the limited effectiveness of each of these procedures has thus limited its use.

The most promising medical device currently available for sleep apnea is nasal continuous positive airway pressure (CPAP). CPAP involves the administration of air under pressure through a nasal mask. Air pressure is measured in centimeters of water (cm $H_2O$), and CPAP typically delivers air to the patient at a pressure of 3.0 to 18 cm $H_2O$. The exact means by which CPAP acts to prevent or reduce sleep apnea is not fully understood. However, CPAP appears to act as a pneumatic splint on the pharyngeal area, that is, the positive air pressure from the CPAP device forces the upper respiratory tract open and prevents collapse of the pharynx and tongue over the air passages. In addition, it is thought that CPAP aids in increasing lung volume which improves the upper airway muscle dilation tone as air is exhaled.

In studies of patients treated with CPAP for sleep apnea, the use of a CPAP device has been found to produce a significant reduction or elimination of apnea, less severe oxygen desaturation during REM sleep, and an increase in the amount of time spent in deeper sleep. Several studies have documented a high rate of patient compliance (85%–95%) with home nasal CPAP systems. CPAP is usually administered initially in the sleep disorders center. After a sleep study is conducted and it is determined that the individual may benefit from CPAP (it is determined that he has either obstructive or mixed apnea), the patient is then fitted with a CPAP device the same or a following night. As the patient starts to obstruct, the CPAP is increased to maintain the airway. This continues through all stages of sleep, including and in particular REM sleep, and is used to determine the CPAP pressure settings for the individual patient which will maintain an open airway.

If CPAP therapy is successful in the sleep lab, the patient is sent home on CPAP therapy with regular follow-ups (either visits to the sleep lab or at-home monitoring) at 6–12 month intervals to assess patient compliance and improvement. When compared to other forms of therapy, the complications with nasal CPAP are relatively minor and include a reduction of sinus draining, drying of the nasal membrane (mucosa), and inflammation of the nasal mucosa (rhinitis). The available data regarding this treatment approach have led many physicians to conclude that CPAP is the best choice for therapy in patients with sleep apnea.

A CPAP device sold under the brand name Tranquility® is described in the brochure entitled "Tranquility®Nasal CPAP System", distributed by Healthdyne Corp., and is designed to eliminate some of the problems inherent in devices using CPAP valves. This device replaces the CPAP valve with a semiconductor pressure transducer and an electronic servo-control system that adjusts blower speed to maintain pressure. The device maintains pressure to calibrated setpoints so that the user knows what pressure would be delivered without having to adjust the machine while measuring the output pressure with an additional device.

SUMMARY OF THE INVENTION

It is an object of the invention to provide a CPAP device which gradually builds up pressure to the prescribed therapeutic level, and which allows the patient to adjust the mask according to the prescribed pressure and then return the CPAP device to a gradual pressure build-up mode.

In accordance with a first aspect of the invention, a device for treating sleep apnea by supplying pressurized air to the nasal passages of a user includes connection means for supplying pressurized air into the nasal passages of the user, generating means for generating pressurized air and for supplying the pressurized air to the connection means, and control means for controlling the pressure level supplied by the generating means. The control means comprises ramp means for selectively controlling the generating means to generate pressurized air at a pressure level which increases for a preset time to the prescribed pressure level, and switch means for overriding the ramp means and for controlling the generating means to immediately generate pressurized air at the prescribed pressure level.

In accordance with another aspect of the invention, the means for overriding comprises a manually operated on-off switch operatively connected to the microprocessor.

In accordance with still another aspect of the invention, the control means comprises a control unit having a digital microprocessor disposed therein. The generating means preferably comprises a blower and a variable speed motor connected to the blower and to the microprocessor. The ramp means preferably comprises a pressure transducer which generates a signal indicative of the pressure produced by the blower and which transmits the signal to the microprocessor.

In accordance with yet another aspect of the invention, the control means controls the motor so that the blower maintains a constant pressure whether the user inhales or exhales.

In accordance with still another aspect of the invention, a monitoring and recalibrating means is provided which preferably comprises a valve which is located between the blower and the pressure transducer and which is controlled by the microprocessor to selectively connect the pressure transducer to the blower or to atmosphere.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The invention is a medical device for treating sleep apnea, specifically a nasal continuous positive airway pressure (CPAP) device. The invention is an improvement over earlier CPAP devices because it produces low resistance to exhalation, generally responds faster to pressure changes, allows pressure to build up gradually, and allows the patient to adjust the mask at the prescribed pressure and subsequently return the device to a gradual pressure build-up mode. The term "mask" as used herein is understood to encompass any other suitable connection means for administration of pressurized air to the patient.

Figure 1:
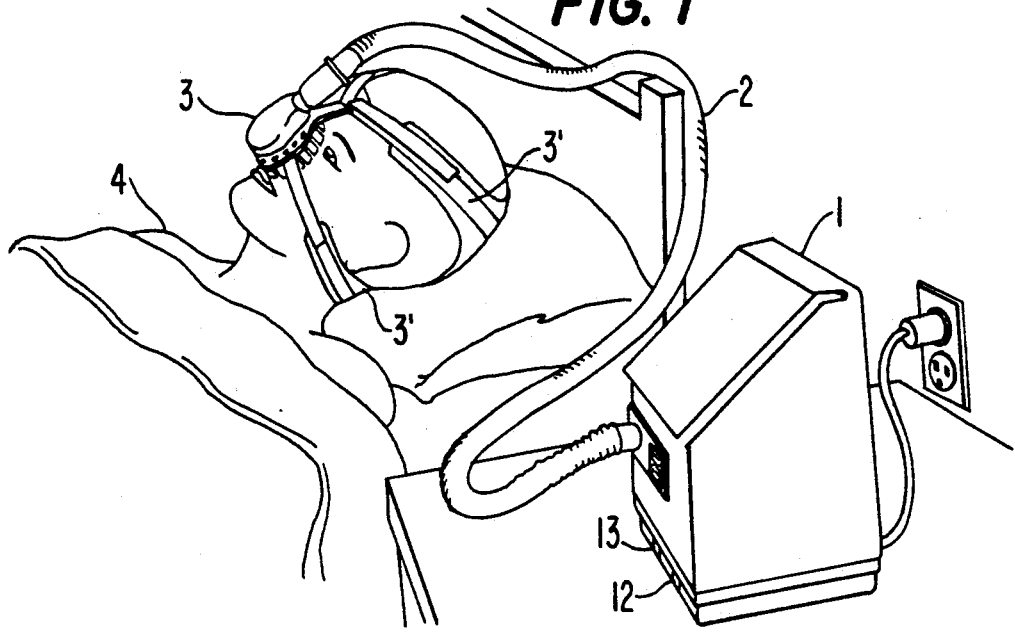
FIG. 1 illustrates a CPAP device constructed in accordance with a preferred embodiment of the invention.

Referring to FIG. 1, a CPAP device comprises a control unit 1, a flexible tube 2, and a suitable device for injecting air into the patient's nasal passages, such as a mask 3 which seals over the patient's nose. The mask 3 preferably includes adjustable straps 3' for adjusting the tightness of the mask on the face of the patient 4.

Figure 2:
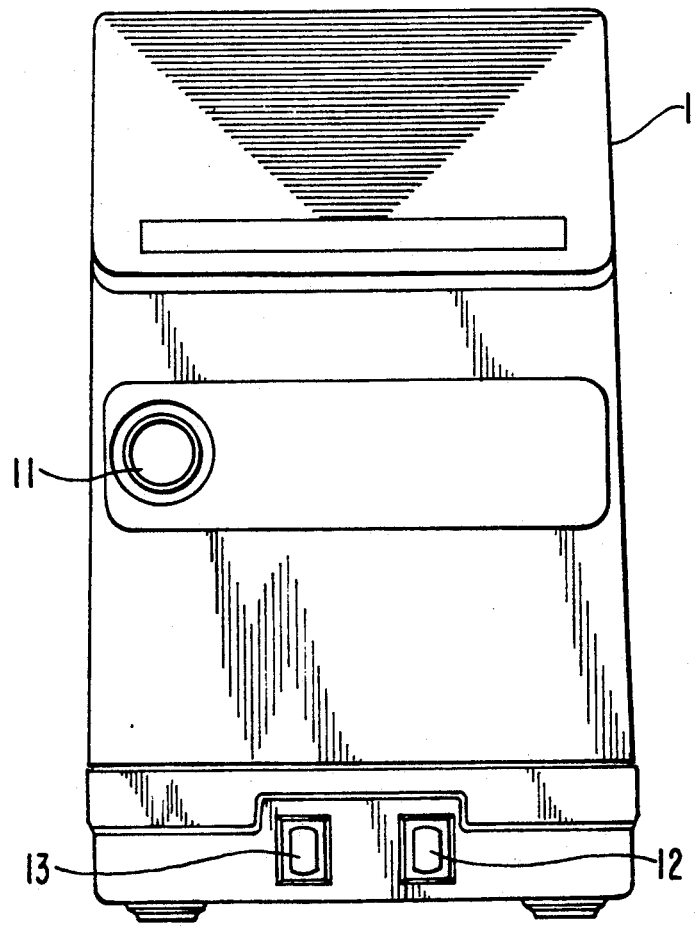
FIG. 2 is a front view of the control unit of FIG. 1.

Referring to FIG. 2, the control unit 1 includes a hose connection 11 which is provided for the hose 2, a power switch 13, and a switch 12, which is provided to test the seal of the mask in a manner discussed in greater detail below. This switch, which will be referred to as a set-to-test switch for the sake of convenience, is illustrated as a simple binary switch.

Figure 3:
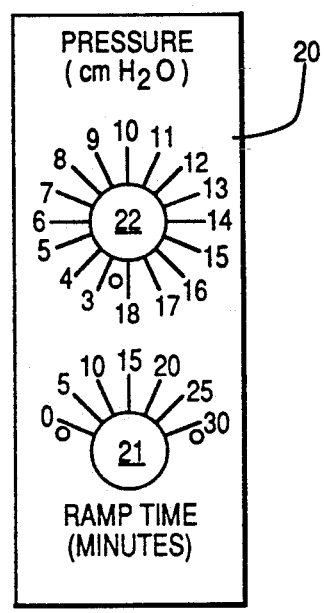
FIG. 3 illustrates the pressure and time control dials of the control unit of FIG. 1.

On the rear of the unit 1 are pressure and ramp time dials, 22, 21 shown in FIG. 3. These dials constitute an important feature of the invention in that they allow the device to gradually increase the pressure to the prescribed level, thereby enabling the patient to fall asleep more easily. A pressure ramp time is adjustable by a suitable amount, e.g. 5 to 30 minutes, via dial 21, and the prescribed pressure of the device is likewise adjustable by a suitable amount, e.g. from 3 to 18 cm $H_2O$, via dial 22. These rotary dials could, of course, be replaced by any suitable devices capable of performing the desired functions, such as sliding switches or a plurality of on-off switches which collectively perform the functions of the dials.

Figure 4:
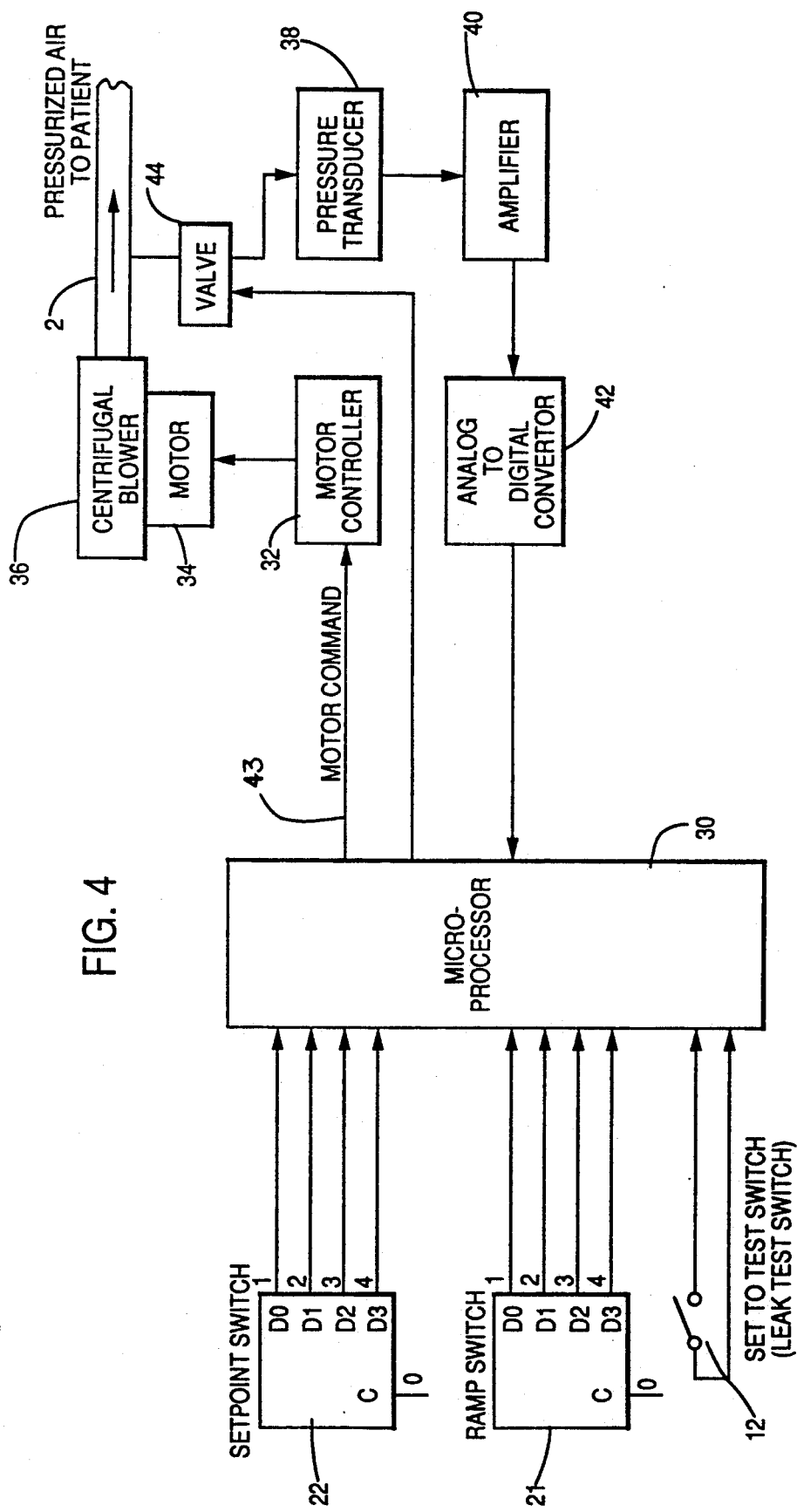
FIG. 4 is a schematic representation of the control device of FIG. 1.

Referring now to FIG. 4, the control unit 1 for the CPAP device preferably includes a variable speed electric motor 34 which drives a centrifugal blower 36 and which is controlled by a motor controller 32. The blower 36 provides pressurized air to the patient through the hose 2. In the preferred embodiment, the pressure is continuously monitored by a pressure transducer 38 which produces an electrical signal which is in turn amplified by the amplifier 40 and digitized by a suitable analog to digital convertor 42. This signal is received by a conventional microprocessor 30. The microprocessor is programmed to implement the ramp function as selected by the dials 21 and 22. The microprocessor also implements the set-to-test feature. The output from the microprocessor is a motor command 43 to the motor controller 32.

Although not essential to the operation of the CPAP device, the preferred microprocessor should be one which is capable of making the necessary and timely motor control corrections. A rapid response time allows the device to maintain a consistent therapeutic pressure in that it allows the CPAP device to promptly react to the patient's breathing pattern. By measuring the pressure at the outlet of blower 36 and thereby detecting any changes in pressure caused by the patient's breathing, the microprocessor 30 can control motor 34 to maintain the pressure constant whether the user is inhaling or exhaling, thus diminishing the uncomfortable sensation of increased pressure usually associated with exhalation.

To assist in maintaining pressure consistency, the microprocessor should be programmed to constantly monitor and recalibrate the pressure transducer. To this effect, a valve 44 is provided in the air line connecting the blower 36 to the pressure transducer 38. This valve is periodically actuated by microprocessor 30 to connect transducer 38 to the atmosphere, at which point the pressure transducer is tested to determine whether or not it correctly reads zero, i.e. atmospheric pressure. For example, if, when valve 44 is actuated, the pressure transducer outputs a reading of 0.1 cm $H_2O$, microprocessor 30 will subtract 0.1 cm $H_2O$ from future readings, thereby ensuring an accurate pressure reading. Following the calibration operation, the microprocessor 30 will deactivate valve 44 so that transducer 38 can resume its normal pressure monitoring operation.

Commercially available microprocessors can be easily programmed to perform the disclosed functions. One such microprocessor is manufactured by Intel Corp. under the part No. N-80C196KB-10.

Although a controller using a digitally controlled programmable microprocessor of the type discussed above is preferred, any system capable of increasing the output pressure at a selected rate up to a predetermined pressure level could be used.

Figure 5:
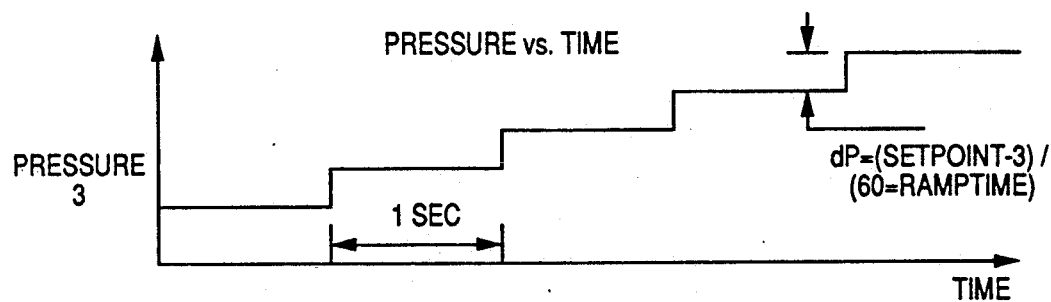
FIG. 5 is a graphical representation of the ramp function.

The gradual increase in pressure (ramp function) is shown graphically in FIG. 5 which shows that the pressure increases constantly, i.e., increases without significant decrease, during the time preset by operation by dial 21. Because the servo system is digital, all the variables are discrete or quantified. Therefore, the ramp is, so far as the control loop is concerned, a series of low amplitude steps each having a height dP in FIG. 5. In the actual implementation the steps are 1 second wide. The pressure step size is dependent on the ramp time and on the selected pressure. In the embodiment of FIG. 3, for example, the steepest ramp is a 5 minute ramp from 3 to 18 cm $H_2O$, and the shallowest ramp is a 30 minute ramp from 3 to 4 cm $H_2O$. The change in pressure dP per unit time for each case, would be 0.05 cm $H_2O$/sec. and 0.0005 cm $H_2O$/sec., respectively. Although the pressure increases are illustrated as discrete steps in FIG. 5, in practice, the steps are not noticeable because they are so small. Furthermore, since the output is a real physical variable and not a discrete value, any slight variations from the quantified level which consequently occur tend to smooth the steps.

A very important feature of the present invention is the provision of the set-to-test switch 12, which enables the patient to test for leaks in the mask 3 and to adjust the mask to eliminate any leaks. A mask which appears to seal tightly at the minimum output pressure of the CPAP device may actually leak excessively at the prescribed pressure, thereby severely degrading the effectiveness of the device. To avoid this problem, the switch 12 is provided which, when pushed a first time, sends a signal to microprocessor 30 which causes the control unit to override the ramp function and to supply pressurized air at the prescribed pressure level previously. The patient can then adjust the mask to ensure that the mask will seal properly at the prescribed pressure. A second press of the switch deactivates the override feature, the pressure decreases, and the ramped increase of pressure is resumed.

Without the provision of this set-to-test feature, the use of a ramped pressure increase in a CPAP device would be severely degraded in that the patient would not be able to assure a proper sealing of the mask until the pressure reaches its prescribed value. However, the primary purpose for employing a ramped pressure increase is to allow the patient to fall asleep before the pressure reaches its prescribed value, which purpose is destroyed if the patient must remain awake to ensure that the mask is properly sealed at the prescribed pressure.

Although the illustrated embodiment utilizes a simple on-off switch as the set-to-test switch 21, it should be understood that any device capable of selectively making and braking an electrical current could be used as the set-to-test switch. For example, a switch which, when pressed once, closes the circuit for a predetermined time interval and then reopens the circuit could be used in place of such an on-off switch.

Furthermore, the "set-to-test" feature is a feature that could be implemented automatically without any switch, e.g. by a program control within the microprocessor. For example, the microprocessor could be programmed to override the ramp at 5 seconds into the operation and to supply the prescribed selected pressure for a period of an additional 5 seconds. After this 5 second interruption, the pressure supplied by the unit would be reduced and the ramped pressure increase would resume.

To use the CPAP device, the device is set-up as shown in FIG. 1 with the patient placing the mask 3 over his nose. The prescribed pressure and ramp time interval are set using the dials 22 and 21. The patient then presses the set-to-test switch 12 and adjusts the mask to ensure an effective sealing at the prescribed pressure. The patient then presses the set-to-test switch a second time, in response to which the pressure supplied by control unit 1 drops to the ramp pressure. The device then begins to gradually increase the pressure over the selected time interval until the prescribed pressure is obtained. When the pressure reaches the prescribed level, the mask will be correctly adjusted to seal properly.

What is claimed is:

1. A device for treating sleep apnea by supplying pressurized air to the nasal passages of a user, comprising:
    (A) connection means for supplying pressurized air into said nasal passages, (B) generating means for generating pressurized air and for supplying said pressurized air to said connection means; and (C) control means for controlling the pressure level supplied by said generating means, said control means comprising ramp means for selectively controlling said generating means to generate pressurized air at a pressure level which constantly increases for a preset time to a prescribed pressure level, and means for overriding said ramp means and for controlling said generating means to immediately generate pressurized air at said prescribed pressure level.

2. The device of claim 1, wherein said control means comprises a control unit having a digital microprocessor disposed therein.

3. The device of claim 2, wherein said means for overriding comprises a manually operated on-off switch operatively connected to said microprocessor.

4. The device of claim 2, wherein said control unit includes manually operated means for selecting said prescribed pressure level and said preset time.

5. The device of claim 4, wherein said manually operated means comprises first and second dials.

6. The device of claim 2, wherein said generating means comprises a blower and a variable speed motor connected to said blower and to said microprocessor, and wherein said ramp means comprises a pressure transducer which generates a signal indicative of the pressure generated by said blower and which transmits said signal to said microprocessor.

7. The device of claim 6, wherein said control means controls said motor so that said blower maintains a constant pressure whether the user inhales or exhales.

8. The device of claim 6, wherein said means for overriding comprises a manually operated on-off switch operatively connected to said microprocessor.

9. The device of claim 6, further comprising means for constantly monitoring and recalibrating said pressure transducer.

10. The device of claim 9, wherein said monitoring and recalibrating means comprises a valve which is located between said blower and said pressure transducer and which is controlled by the microprocessor to selectively connect said pressure transducer to said blower and to the atmosphere.

11. The device of claim 1, wherein said means for overriding comprises a manually operated on-off switch which is adapted to override said ramp means when actuated a first time.

12. The device of claim 11, wherein said switch is adapted to return control of said device to said ramp means when actuated a second time.

13. The device of claim 1, wherein said control means further comprises means for controlling said generating means to generate a pressure which is maintained constant whether the user inhales or exhales.

14. A control device for a device which treats sleep apnea by supplying pressurized air to the nasal passages of a user through a connection device which is connected to said control device through a hose, said control device comprising:

(A) a generating device adapted to pressurize air and to supply the pressurized air to said connection device; and (B) a control device adapted to control the pressure level supplied by said generating device, said control device comprising a ramp generating device adapted to selectively control said generating device to generate pressurized air at a pressure level which constantly increases for a preset time to a prescribed pressure level, and an override device which, when actuated, overrides said ramp generating device and which controls said generating device to immediately generate pressurized air at said prescribed pressure level.

15. The device of claim 14, wherein said control device comprises a control unit having a digital microprocessor disposed therein.

16. The device of claim 15, wherein said override device comprises a manually operated on-off switch operatively connected to said microprocessor.

17. The device of claim 15, wherein said control unit includes a manually operated device for selecting said prescribed pressure level and said preset time.

18. The device of claim 17, wherein said manually operated device comprises first and second dials.

19. The device of claim 15, wherein said generating device comprises a blower and a variable speed motor connected to said blower and to said microprocessor, and wherein said ramp generating device comprises a pressure transducer which generates a signal indicative of the pressure produced by said blower and which transmits said signal to said microprocessor.

20. The device of claim 19, wherein said control device controls said motor so that said blower maintains a constant pressure whether the user inhales or exhales.

21. The device of claim 19, wherein said override device comprises a manually operated on-off switch operatively connected to said microprocessor.

22. The device of claim 19, further comprising a device for constantly monitoring and recalibrating said pressure transducer.

23. The device of claim 22, wherein said monitoring and recalibrating device comprises a valve which is located between said blower and said pressure transducer and which is controlled by the microprocessor to selectively connect said pressure transducer to said blower and to the atmosphere.

24. The device of claim 14, wherein said override device comprises a manually operated on-off switch which is adapted to override said ramp device when actuated a first time.

25. The device of claim 24, wherein said switch is adapted to return control of said device to said ramp device when actuated a second time.

26. The device of claim 14, wherein said control device further comprises means for controlling said generating device to generate a pressure which is maintained constant whether the user inhales or exhales.

27. The device of claim 1, wherein said control means further comprises means for automatically controlling said generating means to continuously generate pressurized air at said prescribed pressure level after said preset time.

28. The device of claim 1, wherein said ramp means controls said generating means to generate pressurized air at a pressure level which increases in a series of discrete steps during said preset time.

29. The device of claim 14, wherein said control device further comprises a device which automatically controls said generating device to continuously generate pressurized air at said prescribed pressure level after said preset time.

30. The device of claim 14, wherein said ramp generating device controls said generating device to generate pressurized air at a pressure level which increases in a series of discrete steps during said preset time.

31. A method of treating sleep apnea by supplying pressurized air to the nasal passages of a user, said method comprising the steps of:
(A) generating pressurized air via a generating device;
(B) supplying said pressurized air into said nasal passages; and
(C) controlling the pressure level of said pressurized air, said controlling step comprising the steps of
  (i) selectively controlling said generating device to generate pressurized air at a pressure level which constantly increases for a preset time to a prescribed pressure level, and
  (ii) overriding said step (i) and controlling said generating device to immediately generate pressurized air at said prescribed pressure level.

* * * * *